United States Patent [19]

Sisto et al.

[11] Patent Number: 4,748,155
[45] Date of Patent: May 31, 1988

[54] PHARMACOLOGICALLY ACTIVE TRIPEPTIDES AND PROCESS FOR THEIR SYNTHESIS

[75] Inventors: Alessandro Sisto, Rome; Antonio S. Verdini, Monterotondo; Antonio Virdia, Rome; Giovanna De Luca, Rome; Giovanni Di Stazio, Rome; Vincenzo Politi, Rome, all of Italy

[73] Assignees: Eniricerche S.p.A., Milan; Polifarma S.p.A., Rome, both of Italy

[21] Appl. No.: 838,120

[22] Filed: Mar. 10, 1986

[30] Foreign Application Priority Data

Mar. 19, 1985 [IT] Italy ................... 19961 A/85

[51] Int. Cl.[4] .................. A61K 37/43; C07K 5/08
[52] U.S. Cl. ........................... 514/18; 530/331
[58] Field of Search .................. 530/332; 514/18

[56] References Cited

U.S. PATENT DOCUMENTS 3,876,624  4/1975  McGregor ................. 530/332
4,638,046  1/1987  Verdini et al. ............. 530/332

OTHER PUBLICATIONS

Chem. Abstr., vol. 105, (1986), 108710.
Chem. Abstr., vol. 95, (1981), 43627.

*Primary Examiner*—Delbert R. Phillips
*Attorney, Agent, or Firm*—Hedman, Gibson, Costigan & Hoare

[57] ABSTRACT

Pharmacologically active tripeptides, with at least a retro-inverted peptidic bond, definable by means of the following general formulae:

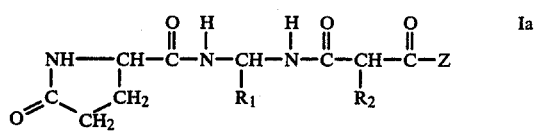

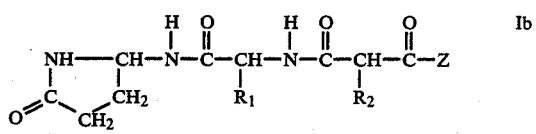

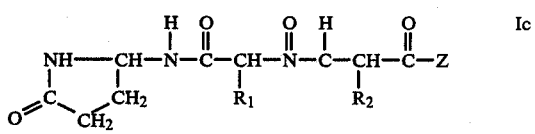

their pharmaceutically acceptable salts, esters or alkyl amides, wherein $R_1$ represents a hydrogen atom, an alkyl group with a maximum of 7 carbon atoms, an aryl, hydroxyalkyl or hydroxyarylalkyl, guanidylalkyl, amino-alkyl, alkyloxy-alkyl, acylamino-alkyl, imidazolylalkyl, indolylalkyl, mercapto alkyl, alkylmercaptoalkyl, carbamoyl-alkyl, carboxyalkyl, alkyl-carbamoylalkyl or alkyloxy-carbonylalkyl group;

$R_2$ represents a

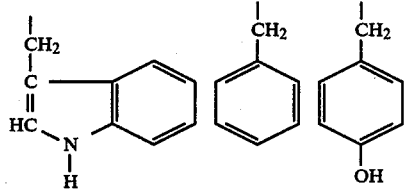

group,

Z is an $OH$, $OR_3$, $NH_2$, $NHR_3$ group, wherein
  $R_3$ represents an alkyl group with a number of carbon atoms comprised within the range of from 1 to 10.

8 Claims, No Drawings

PHARMACOLOGICALLY ACTIVE TRIPEPTIDES AND PROCESS FOR THEIR SYNTHESIS

The present invention relates to novel pharmacologically active tripeptides, with at least a retro-inverted peptidic bond, their pharmaceutically acceptable salts, esters or alkyl amides, definable by means of the following formulae:

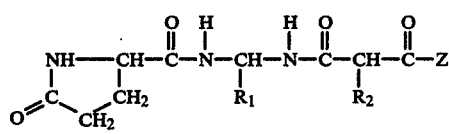

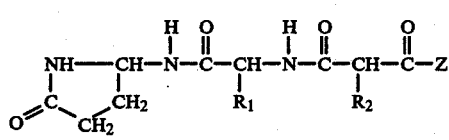

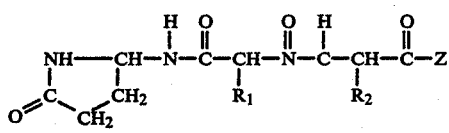

wherein
$R_1$ represents a hydrogen atom, an alkyl group with a maximum of 7 carbon atoms, an aryl, hydroxyalkyl or hydroxyarylalkyl, guanidylalkyl, amino-alkyl, alkyloxy-alkyl, acylamino-alkyl, imidazolylalkyl, indolylalkyl, mercapto alkyl, alkylmercaptoalkyl, carbamoylalkyl, carboxyalkyl, alkyl-carbamoylalkyl or alkyloxycarbonylalkyl group;
$R_2$ represents a

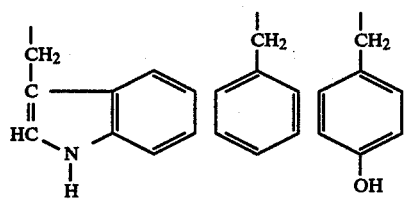

$Z$ is a OH, $OR_3$, $NH_2$, $NHR_3$ group, wherein $R_3$ represents an alkyl group with a number of carbon atoms comprised within the range of from 1 to 10.

The Italian Patent Application IT 49574 A/83 discloses and claims a tripeptide with aminoacidic sequence Glp-Leu-Trp-OH and analogues thereof with hypotensive, tranquilizer and analgesic action. Glp-Leu-Trp-OH tripeptide is a part of the sequence of a decapeptide from natural origin isolated from the poison of Crotalus atrox snake.

Said tripeptide and the analogues thereof, active as hypotensive agents, can be used in therapy for the treatment of all hypertensive states.

However, the use of said compounds suffers from limitations.

So, e.g., in the pharmaceutical and clinical field, they are scarcely used due to their lability, in vivo, to the action of peptidasic enzymes.

Said enzymes, present in circulus, degrade indeed the tripeptide and the analogues thereof to inactive fragments.

It has been found now that, by retro-inverting at least one of the peptidic bonds of said tripeptides, new tripeptidic analogues free from the above mentioned drawbacks are obtained.

The retro-inversion of peptidic bond, where by this term the inversion of peptidic bond direction is meant, allows indeed tripeptidic analogues to be obtained which, even if are not exactly identical, from a topochemical viewpoint, to natural peptides to which reference is made, maintain their pharmacological activity and, advantageously, show a longer stability in vivo to the action of peptidases.

Accordingly, the purpose of the present invention are pharmacologically active tripeptides, with at least a retro-inverted peptidic bond, their pharmaceutically acceptable salts, esters or alkyl amides, definable by means of the following formulae:

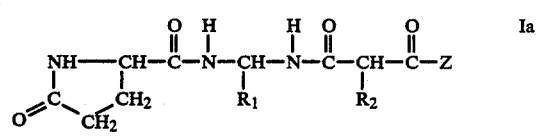

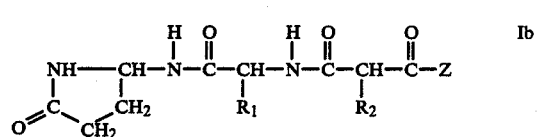

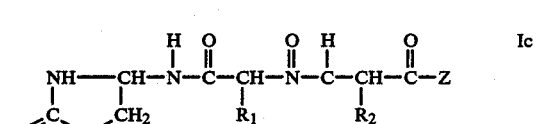

wherein $R_1$, $R_2$ and $Z$ have the hereinabove reported meaning. According to a preferred form of embodiment, tripeptides are synthesized of formula (Ia), Ib and Ic, wherein $R_1$ is

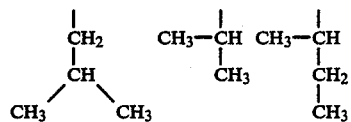

and $R_2$ and $Z$ have the hereinabove reported meaning.

Particularly preferred are tripeptides (Ia), (Ib) and (Ic),
wherein
$R_1$ is

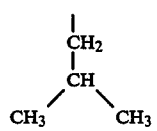

$R_2$ is

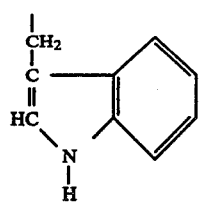

and Z has the hereinabove reported meaning.

The retro-inversion of peptidic bonds is carried out according to known techniques.

The inversion of one single peptidic bond in the sequence involves the transformation of the two aminoacidic residues forming the inverted bond.

In particular, in tripeptides of formula (Ia), wherein the bond in position 2 is retroinverted, the aminoacidic residue:

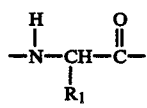

is transformed into a geminal diamino residue:

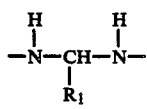

wherein R has the hereinabove reported meaning, and the aminoacidic residue

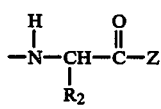

is converted into a 2-substituted malonyl residue

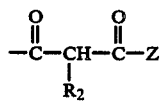

wherein $R_2$ and Z have the hereinabove reported meaning.

In tripeptides of formula (Ib), wherein the peptidic bond 1 and 2 are retro-inverted, the aminoacidic residue

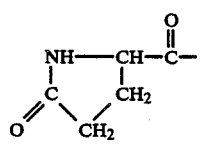

is transformed into a geminal diaminic residue

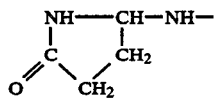

and the aminoacidic residue

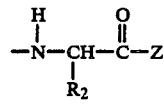

is transformed into a 2-substituted malonyl residue

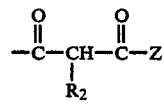

wherein $R_2$ and Z have the hereinabove indicated meaning.

The intermediate aminoacidic residue has a D-configuration,

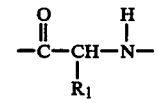

In tripeptides of formula (Ic), wherein the peptidic bond 1 is retroinverted, the aminoacidic residue

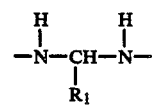

is converted in a geminal diaminic residue

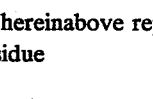

and the aminoacidic residue

-NH-CH-C-
   |   ||
   R₁  O is transformed into a 2-substituted malonyl residue

O       O
   ||      ||
-C-CH-C-
   |
   R₁ wherein $R_1$ has the hereinabove indicated meaning.

The geminal diaminic residue has in the tripeptides of the present invention an S-configuration, whilst the 2-substituted malonyl residue has an R and/or S configuration. According to the present invention, the tripeptides of general formula (Ia) are prepared by condensation induced by dicyclohexylcarbodiimide (DCCI) and N-hydroxybenzotriazole (HOBt) between the peptidic fragment of general formula

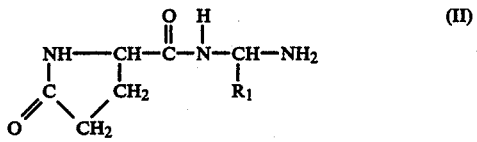

wherein $R_1$ has the hereinabove indicated meaning, and a 2-substituted malonyl derivative of formula

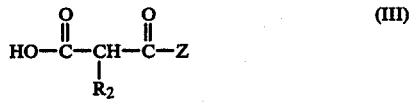

wherein $R_2$ and Z have the hereinabove reported meaning.

The tripeptides of general formula (Ib) are prepared by condensation induced by DCCI and HOBt between the peptidic fragment of general formula

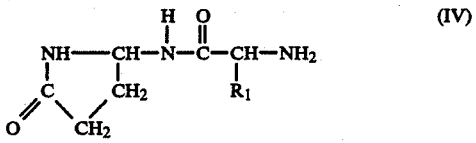

wherein $R_1$ has the hereinabove reported meaning, and a 2-substituted malonyl derivative of general formula (III).

According to the present invention, the tripeptides of general formula (Ic) are prepared by condensation induced by DCCI and HOBt between the geminal diaminic residue

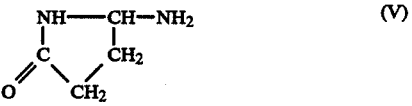

and the peptidic fragment of general formula

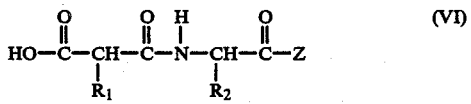

wherein $R_1$, $R_2$ and Z have the hereinabove reported meaning.

Aminic, hydroxy, carboxy, carboxyamide, indole, imidazole, guananidine and mercapto functions possibly present in $R_1$, $R_2$ or Z are suitably protected by means of temporary protecting groups normally used in syntheses of peptides.

According to the present invention, the peptidic compounds of general formula (II), (IV) and (VI) are prepared by using one of the techniques known in the synthesis of peptides.

Such preparations are typically carried out according to what described by Badauszky, M. and Ondetti, M.A., Peptyde Snythesis, Interscience, New York, 1976 and Peptides, vol. I, Gross and Meienhofer, J. Editor, Academic Press, New York, 1979.

The tripeptides of formula (Ia), (Ib) and (Ic) are obtained as an equimolecular mixture of the two R and S isomers. At the end of condensation reactions, the temporary protecting groups are removed, and the isomers are then isolated by means of processes known such as, e.g., extractions, distribution in counter-current, precipitation, crystallization or chromatography.

In the preferred form of embodiment, the two isomers are separated by reverse-phase high pressure preparative liquid chromatography, using Lichroprep RP-18 25–40 $\mu$ (Merck) as the stationary phase, and 0.1% trifluoroacetic acid (TFA) and 28% $CH_3CN$ in water as the eluant.

The fractions corresponding to each individual peak are then combined, concentrated under reduced pressure, and freeze-dried.

The purity of so-obtained compounds is checked by means of reverse phase high pressure chromatographic analysis (RP-HPLC), using a Perkin-Elmer Chromatograph with Hybar ® column, 250×4 mm, with Lichrosorb RP-18 10 micron (Merck) packing and, as the movable phase, a mixture (A) of 90% $CH_3CN$, 0,1% TFA in water, and a mixture (B) of 10% $CH_3CH$, 0.1% TFA in water.

An elution with linear gradient of from 20% of A to 65% of A over 25 minutes has been used.

The purity of tripeptides is moreover tested by means of thin-layer chromatography (TLC) in silica gel, using the following eluant systems: n-butanol:acetic acid:water (BAW) (4:1:1) and chloroform:methanol:acetic acid (CMA) (85:10:5).

The hypotensive activity of the tripeptides of the present invention has been tested on the arterial pressure of normotensive male rats of C.D: strain from Charles River Co., of weight of 200–300 g, anaesthetized with urethane. After tracheal cannulating, the right-hand carotid artery is isolated and connected by a cannula to a Hewlett-Packard model 1280 pressure transducer.

From isolated left-hand carotid the arterial flow is recorded by means of Biotronex Model BL610 electromagnetic flowmeter.

On Hewlett Packard Model 8824-C polygraph, such parameters as dp/dt (pressure variation with time), ECG (electrocardiogram) and BPM (beats per minute) are recorded.

The so-tested tripeptides cause a gradual and long-lasting hypotensive effect which reaches, at the dosage of 0.2 mg/kg, for diastolic arterial pressure, a delta of from 25 mmHg to 35 mmHg, and for systolic arterial pressure, a delta of from 20 mmHg to 40 mmHg.

The tranquilizer activity has been tested by the "Activity Cage" test. By this test, the motorial activity is measured of treated animals, compared to that of control animals. Before administering the substance under test, during 4 consecutive days the basal motorial activity (from 10 o'clock to 16 o'clock) is recorded of male mice, albino Swiss strain, weight of 25–28 g, fasting since 8 o'clock. The basal value is that obtained from the average over 4 days. The compounds under test, injected at the dosage of 10 mg/kg/ip, show an inhibition between 30 and 40% of basal motorial activity.

The analgesic activity has been tested by means of the writhing test. As the painful agent, an aqueous solution of acetic acid at 3% was used, injected by intraperitoneal way (0.1 ml/10 g), and the number was recorded of animal' writhings during the observation time of 20 minutes. The compounds under test, injected at the rate of 10 mg/kp i.p., show a inhibition of the number of contractions, comprised within the range of from 15 to 30%.

The tripeptides of the present invention form basic salts with several inorganic and organic bases, which too are within the scope of the present invention.

Such salts comprise: ammonium salts, salts of alkaline metals, such as sodium and potassium salts, salts of alkaline-earth metals, such as calcium and magnesium salts, salts with organic bases, such as, e.g., dicyclohexylamine, benzathine, N-methyl-glucamine, hydrabamine salts, salts with aminoacids such as arginine, lysine, and the like.

Preferably non-toxic salts acceptable from the physiological view point are prepared, such as, e.g., potassium or sodium salts, and salts of aminoacids.

These and the other not physiologically acceptable salts can be used, e.g., in the isolation and in the purification of the tripeptides of the present invention.

The salts are prepared by conventional methods, by reacting the tripeptide in the acid form with 1 or more equivalents of a proper base.

The reaction is carried out in a liquid medium, in the presence of a solvent selected among those in which the salt formed is insoluble, or in the presence of water, subsequently removed under vacuum.

The tripeptides of the present invention, and their pharmaceutically acceptable basic salts are used as hypotensive agents.

The hypertension can be alleviated in all mammalian species, including man, by means of the administering of a composition containing a tripeptide of general formula (Ia), (Ib) or (Ic), or a combination thereof.

To the purpose of reducing blood pressure, a single dosage is suitable, or preferably, from 2 to 4 daily subdivided dosages, on a basis of about 0.1–400 mg/kg of body weight per day, preferably of from 2 to 300 mg/kg of body weight per day can be used.

The tripeptides according to the present invention can be administered by oral way, as pharmaceutical formulations such as, e.g., tablets, capsules, granulates, drops or syrups; by parenteral way, e.g., subcutaneous, intramuscular, intravenous or intraperitoneal way, as sterile solutions or suspension.

The tripeptides of the present invention are formulated by mixing about 10–500 mg of a tripeptide, or of a mixture of tripeptides of formula (Ia), (Ib) or (Ic), with a substance selected among an aromatizer, a carrier, a binding agent, a preserver, a stabilizer, or a supporting substance, acceptable from the physiological viewpoint, in a form of unitary dosage, according to what required by the usual pharmaceutical art.

The amount of active substance in these compositions or preparates is such as to obtain a dosage proper and within the range of above-reported values.

The tripeptides of the present invention can be formulated in combination with a diuretic.

Diuretics suitable to that purpose are selected among hydrochlorothiazide, chlorothiazide, flumethiazide, hydroflumethiazide, bendroflumethiazide, metochlorothiazide, trichlorothiazide, polythiazide or benzthiazide, ethacrynic acid, tricrinophen, chlorthalidone, furosemide, musolimine, bumetanide, triamterene, amiloride or spironolactone.

The amount of active substance in these compositions is such as to obtain a suitable dosage within the range of values indicated for the various administering modalities, whereas the amount of diuretic varies within the range of from 15 to 300 mg/day, preferably of from 15 to 200 mg.

In the hereinunder reported descriptions of syntheses, the following abbreviations are used: Z=benzyloxycarbonyl; $Et_2O$=ethyl ether; DMF=dimethylformamide; EtOAc=ethyl acetate; HOBt=N-hydroxy-benzotriazole; DCCI=dicyclohexylcarbodiimide; DCU=dicyclohexylurea; TFA=trifluoroacetic acid; BTI=1,1-bis[(trifluoroacetoxy)]iodobenzene; HOSu=N-hydroxysuccinimide.

The following experimental examples are illustrative and not limitative of the invention.

EXAMPLE 1

(A) Synthesis of pyroglutamyl-leucinamide (Glp-Leu-NH$_2$)

10.0 mmol (1.29 g) of pyroglutamic acid are dissolved in 15 ml of DMF, and to the solution 12.0 mmol (1.75 g) of HOBt and 11.0 mmol (2.27 g) of DCCI dissolved in 15 mml of DMF are added.

The reaction mixture is maintained, under slow stirring, at 0° C. for 30 minutes, and at room temperature (20°–25° C.) for further 30 minutes.

To said mixture 10.0 mmol (1.66 g) of hydrochloride of the amide of leucine and 10.0 mmol (1.01 g) of N-methyl-morpholine (NMM) dissolved in 30 ml of DMF are then added.

After two hours of reaction at room temperature, precipitated DCU is filtered off, and the reaction mixture is then concentrated to dryness. The so-obtained solid residue is extracted three times, each time with 15 ml of water, and the aqueous extracts so obtained are combined and subsequently extracted three times with 25 ml of EtOAc.

The solvent is evaporated off, and the aqueous solution is treated for 12 hours with 200 ml of ion exchange resin Bio-Rad ® AG-501.x8(D) under stirring. At the end of said time period, the resin is filtered of from the reaction mixture, and is washed with water.

The aqueous solution combined with washing water is concentrated to dryness under reduced pressure, and the remaining solid residue is triturated with 100 ml of $Et_2O$.

The product so obtained, in an amount of 1.76 g (yield 73%), as a finely subdivided white powder, at chromatographic (TLC and HPLC) analysis does not show traces of impurities, and $^1$H-n.m.r. spectrum confirms molecule's structure.

The compound shows a melting point (M.P.) of 167° C.–168° C. and $[\alpha]_D^{24}$=+19.0° (c 0.5 in MeOH).

HPLC: $T_r$=3'.

(B) Synthesis of N-(pyroglutamyl)-(S)-1,1-diamino-isopentane trifluoroacetate. (Glp-gLeu-H.TFA)

To 10 ml of acetonitrile containing 5.18 g (12.0 mmol) of 1,1-bis-[(trifluoroacetoxy)]-iodobenzene (BTI) kept under strong stirring, and under nitrogen atmosphere, 50 ml are added of a mixture of $CH_3CN$—$H_2O$ (3:2 v/v) containing 2.41 g (10.0 mmol) of Glp-Leu-NH$_2$.

The reaction is carried out at 25 C for about 3 hours. The solvent is then evaporated to dryness and the oily residue so obtained is triturated with 100 ml of $Et_2O$, is filtered and dried. 2.84 g of product are obtained (yield 87%).

At the chromatographic (TLC and HPLC) analysis the compound does not show impurity traces, and $^1$H-n.m.r. spectrum confirms molecule's structure. The compound shows:

M.P. = 57°–61° C.
$[\alpha]_D^{24} = -25.0°$ (c 1.5 in MeOH).
TLC (CMA) $R_F = 0.2$.

(C) Synthesis of N-(pyroglutamyl)-N'-[(R,S)-alpha-carboethoxy-beta-3-indolyl-propanoyl]-(S)-1,1-diamino-isopentane. (Glp-gLeu-(R,S)-m-Trp-OEt)

2.47 g (100 mol 9 of Et0-mTrp-OH are dissolved in 15 ml of DMF and, to the solution cooled at 0° C. and kept under strong stirring, 1.75 g (12.0 mmol) of HOBt and 2.26 g (11.0 mmol) of DCCI dissolved in 30 ml of DMF are added.

The reaction mixture is kept at 0° C. under stirring for 30 minutes, and at room temperature (20°–25° C.) for further 30 minutes.

At the end of said time period, to the mixture a solution (25 ml) of DMF containing 2.95 g (9 mmol) of Glp-gLeu-H.TFA and 0.90 g (9 mmol) of NMM is added.

The reaction mixture is maintained, under stirring, at room temperature, until the compound Glp-gLeu-H.TFA disappears, as detected by TLC.

At the end, the reaction mixture is filtered and dried.

The so-obtained solid residue is resuspended with 50 ml of EtOAc, and filtered to separate residual DCU. The so-obtained solution is kept in contact, under stirring, 30 minutes with 30 ml of a solution of sodium bicarbonate at 10%, and finally with 30 ml of a saturated sodium chloride solution.

The organic solution is then dried over magnesium sulphate, filtered and concentrated to dryness. The solid residue is triturated with 50 ml of Et$_2$O, the product being obtained in an amount of 3.17 g (yield 69%) as a finely subdivided powder.

The chromatographic (TLC and HPCL) analysis does not show impurity traces, and $^1$H-n.m.r. spectrum confirms molecule's structure.

M.P. = 174°–176° C.
$[\alpha]_D^{24} = -90.0°$ (c 1.1 in MeOH)
TLC (BWA) $R_F = 0.58, 0.62$
TLC (CMA) $R_F = 0.55$
HPLC: $T_R = 11.5'$ and $11.8'$.

(D) Synthesis of N-(pyroglutamyl)-N'-[(R,S)-alpha-carboxy-beta-3-indolyl-propanoyl]-(S)-1,1-diamino-isopentane. Glp-gLeu-(R,S)-m-Trp-(OH) (Ia)

4.56 g (10.0 mmol) of Glp-gLeu-(R,S)-m-Trp-OEt are dissolved in 20 ml of a dioxane-water mixture (4:1 v/v).

The hydrolysis reaction is carried out at 25° C. for 15 hours, maintaining ph value at 12, by means of repeated additions of a 1M NaOH-dioxane (1:1 v/v) mixture. After having verified the disappearing of the starting product, the reaction mixture is made neutral with diluted (0.1N) HCl, and, after having been diluted with water, is freeze-dried.

The two epimers R and S are isolated by high-pressure preparative liquid chromatography with the stationary phase being constituted by Lichroprep Rp-18 25–40μ (Merck) resin, using 0.1% TFA and 28% CH$_3$CN in water as the eluant. The fractions corresponding to each individual peak are combined, concentrated under reduced pressure, and freeze-dried.

The chromatographic (TLC and HPLC) analysis of the two isolated products does not show impurity traces, and $^1$H-n.m.r. spectrum confirms molecule's structure.

S-isomer:
M.P. = 144°–147° C.
$[\alpha]_D^{24} = -60.0°$ (c 0.4 in MeOH)
TLC (CMA) $R_F = 0.15$
HPLC: $T_R = 4'$.

R-isomer:
M.P. = 154°–157° C.
$[\alpha]_D^{24} = +56.0°$ (c 0.5 in MeOH)
TLC (CMA) $R_F = 0.1$
HPLC: $T_R = 5'$

EXAMPLE 2

(A) Synthesis of N-(N-benzyl-oxycarbonyl-D-leucyl)-S-2-amino-5-pyrrolidone. ("L"-gGlp-D-Leu-Z)

To 50 ml of a mixture of DMF containing 5.30 g (20.0 mmol) of Z-D-Leu-OH, cooled at 0° C. and kept under strong stirring, 3.50 g (24.0 mmol) of HOBt and 4.12 g (22.0 mmol) of DCCI are sequentially added. The mixture, kept stirred, is maintained at 0° C. for 30 minutes and at room temperature for further 30 minutes. At the end of said time period, 25 ml of DMF containing 2.61 g (18.0 mmol) of gGlp-H-HCOOH and 2.02 g (18.0 mmol) of NMM are added.

The reaction is carried out at room temperature for 12 hours.

After having verified the disappearing of starting product gGlp-H-COOH, precipitated DCU is filtered, and the filtrate is concentrated to dryness.

The so-obtained oily residue is resuspended with 100 ml of EtOAc and extracted three times, each time with 25 ml of an aqueous solution at 5% of NaHCO$_3$, and three times, each time with 25 ml of a sodium chloride saturated solution.

The organic extract is concentrated to dryness and the oily residue obtained is triturated with n-hexane. 4.31 g (yield 69%) of product are obtained. The chromatographic (TLC and HPLC) analysis does not show traces of impurities, and $^1$H-n.m.r. spectrum confirms molecule's structure.

TLC (CMA) $R_F = 0.5$
HPLC: $T_R = 13.5'$.

(B) Synthesis of N-(D-leucyl)-S-2-amino-5-pyrrolidone formate. ("L"-gGlp-D-Leu.HCOOH)

To 4.16 g (12 mmol) of "L"-gGlp-D-Leu-Z in 40 ml of DMF, 1.51 g (24.0 mmol) of ammonium formate in 80 ml of MeOH and 1.0 g of a catalyst consisting of palladium at 10% by weight on charcoal are added.

The resulting suspension is kept stirred at room temperature (20°–25° C.) for 30 minutes.

At the end of said time period, the catalyst is filtered off, the solvent is evaporated to dryness, and the oily residue is resuspended with dioxane and is freeze-dried.

3.19 g (100%) are obtained of solid and fluffy product which at the chromatographic (TLC and HPLC) analysis does not show impurity traces.

$^1$H-n.m.r. spectrum confirms molecule's structure.

(C) Synthesis of
N-[(R,S)-alpha-carboethoxy-beta-3-indolyl-propanoyl-D-leucyl]-(S)-2-amino-5-pirrolydone.
("L"-gGlp-D-Leu-(R,S)-m-Trp-OEt)

To 40 ml of a solution of DMF containing 2.87 g (11 mmol) of HO-(R,S)-m-Trp-OEt, 1.75 g (12.0 mmol) of HOBt and, after having cooled the solution to 0° C., 10 ml of DMF containing 2.26 g (1.10 mmol) of DCCI are added.

To said solution, kept under stirring at 0° C. for 30 minutes, and at room temperature for further 30 minutes, 2.59 g (10 mmol) of gGlp-D-Leu-H.HCOOH and 1.01 g (10 mmol) of NMM are added.

After 2 hours of reaction, precipitated DCU is filtered off, and the solvent is evaporated to dryness. The so-obtained residue is resuspended with 100 ml of EtOAc and then sequentially extracted three times, each time with 25 ml of sodium bicarbonate at 5%, and three times, each time with 25 ml of a saturated sodium chloride solution.

The organic extract is dried over magnesium sulphate, filtered and concentrated again to dryness. The so-obtained oily residue is triturated with an $Et_2O$/n-hexane (70:30 v/v) mixture.

The product, obtained in an amount of 4.019 g (yield 87%) as white powder, at chromatographic (TLC and HPLC) analysis does not show impurity traces, and the $^1$H-n.m.r. spectrum confirms molecule's structure.

TLC (CMA) $R_F$=0.65
HPLC: $T_R$=11.8' and 12.5'

(D) Synthesis of
N-[(R,S)-alpha-carboxy-beta-3-indolylpropanoyl-D-leucyl]-(S)-2-amino-5-pyrrolidone.
("L"-gGlp-D-Leu-(R,S)-m-Trp-OH (Ib)

3.66 g (8.0 mmol) of gGlp-D-Leu-(R,S)-mTrp-OEt are dissolved in 100 ml of a dioxane-water (4:1 v/v) mixture.

The resulting solution is maintained, under stirring, at room temperature, at pH 12, for 9 hours.

At the end of the said time period, the solution is made neutral with diluted (0.1N) HCl, and is diluted with water.

The solvent is evaporated to dryness, the residue is resuspended with water and is freeze-dried. The two epimers R and S are isolated by high-pressure preparative liquid chromatography with stationary phase of Lichroprep ® RP-18 25–40μ (Merck), using 0.1% TFA, 28% $CH_3CN$ in water as the eluant.

The fractions corresponding to each individual peak are combined, concentrated under reduced pressure, and freeze-dried.

The two isomers isolated do not show traces of impurities at chromatographic (TLC ad HPLC) analysis, and $^1$H-n.m.r. spectrum confirms molecule's structure.

S-isomer:
TLC (CMA) $R_F$=0.27
HPLC: $T_R$=7.1'
R-isomer:
TLC (CMA) $R_F$=0.22
HPLC: $T_R$=8'

EXAMPLE 3

(A) Synthesis of ethyl
α-carbo-t-butyloxy-β-isopropylpropanoate
(EtO-m-Leu-OBu$^t$)

5.40 g (25 mmol) of EtO-m-Leu-OEt are dissolved in 50 ml of EtOH.

To said solution kept stirred and maintained at a temperature of 0° C., by dropping funnel, 15 ml are added of an EtOH solution containing 1.34 g (24.0 equivalents) of KOH.

The solution is made react for 12 hours, under stirring, at 25° C. At the end of said time period the solvent is evaporated off and the residue, resuspended with 100 ml of water, is extracted three times, each time with 15 ml of $Et_2O$.

The aqueous solution is then made acid to pH 2 with diluted (0.1N)HCl, and is extracted three times, each time with 15 ml of EtOAc.

The combined organic extracts are extracted three times with 10 ml of saturated NaCl solution, and dried over magnesium sulphate.

The solvent is removed by reduced pressure, a thick and colourless oil being obtained, which is resuspended with 50 ml of $CH_2Cl_2$.

To said solution, cooled at −80° C., 2.5 ml of concentrated (98%) $H_2SO_4$ and 4.29 g (75 mmol) of isobutene are added.

The solution is heated to room temperature, and kept stirred over 56 hours.

The preparation is then continued by adding 100 ml of water, and concentrating the volume under reduced pressure.

The so-obtained aqueous solution is extracted three times, each time with 50 ml of $Et_2O$.

The combined organic extracts are extracted with a solution at 5% (by weight) of $NaHCO_3$ and with a saturated NaCl solution, and are then dried over magnesium sulphate.

From the so-obtained residue the solvent is removed under reduced pressure, a thick and colourless oil being obtained in an amount of 4.88 g (yield 80%). At the chromatographic (TLC and HPLC) analysis the compound does not show traces of impurities, and $^1$H-n.m.r. spectrum confirms the structure of the molecule.

TLC (CMA) $R_F$=0.9
HPLC $T_R$=29'

(B) Synthesis of
α-carbo-t-butyloxy-β-isopropyl-propanoic acid.
(HO-m-Leu-OBu$^t$)

4.88 g (20.0 mmol) of EtO-m-Leu-OBu$^t$ are dissolved in 50 ml of EtOH.

The solution, kept stirred, is maintained at a temperature of 25° C. for about 4 hours. During the hydrolysis reaction, solution's pH is maintained at the value of 12.5 by means of sequential additions of 2N KOH in EtOH.

At the end of said time period, the reaction mixture is dried, and the residue is resuspended with 100 ml of water, and extracted three times, each time with 15 ml of $Et_2O$.

The so-obtained aqueous solution is made acid at pH 3 with diluted (0.1N) HCl, and is then extracted three times, each time with 50 ml of EtOAc.

The combined organic extracts are dried over magnesium sulphate, and concentrated to dryness.

A thick and colourless oil is obtained in an amount of 3.15 (yield 73%) which, at the chromatographic (TLC and HPLC) analysis, does not show traces of impurities.

TLC (CMA) $R_F=0.85$
HPLC $T_R=26.5'$ (C) Synthesis of methyl N-(α-carbo-t-butyloxy-β-isopropylpropanoyl)-tryptophanate. (Bu$^t$O-m-Leu-Trp-OMe) 3.22 g (15.0 mmol) of Bu$^t$-O-m-Leu-OH are dissolved in 30 ml of DMF and to the solution, stirred and cooled at 0° C., 26.2 g (18.0 mmol) of HOBt and 3.39 g (16.5 mmol) of DCCI are added.

The solution, while being stirred, is kept at 0° C. for 30 minutes, and at room temperature (20°–25° C.) for further 30 minutes.

At the end of said time period, a solution (30 ml) is added of DMF, containing 3.04 g (12 mmol) of HCl-H-Trp-OMe, and 1.22 g (12 mmol) of NMM, and the reaction is made proceed at room temperature for 12 hours. The preparation is then continued by filtering off precipitated DCU, and drying the reaction mixture. The so-obtained oily residue is resuspended with 100 ml of EtOAc and is subsequently extracted with 45 ml of solution at 5% at NaHCO$_3$, 45 ml of water, 45 ml of 0.1N HCl, and 45 ml of water.

The organic extract is then concentrated to dryness, a thick and slightly yellow-coloured oily residue being obtained. The desired product is isolated from oily residue by means of preparative chromatography on silica gel, using chloroform as the eluant. 3.1 g are so obtained (yield 62%) of a compound, which at the chromatographic (TLC ad HPLC) analysis does not show traces of impurities, while $^1$H-n.m.r. spectrum confirms molecule's structure.

TLC (CMA) $R_F=0.75$
HPLC $T_R=26'$.

(D) Synthesis of N-[methyl N-(R,S)-α-carbo-β-isopropylpropanoyl)-tryptophanate]-(S)-5-amino-2-pyrrolidone. ("L"-g-Glp-(R,S)-m-Leu-Trp-OMe)

2.91 g (7.0 mmol) of HO-m-Leu-Trp-OMe, obtained by acidic hydrolysis of corresponding t-butyl-ester with 4N HCl in dioxane are dissolved in 40 ml of DMF.

To the solution, cooled at 0° C. and kept under strong stirring, 0.966 g (8.4 mmol) are added of HOSue and 1.44 g (7 mmol) of DCCI.

The reaction mixture is kept, while being stirred, at 4° C. for 12 hours, and to it 1.22 g (8.4 mmol) of g-Glp-H.COOH and 0.848 g (8.4 mmol) of NMM are added.

The reaction is carried out under stirring at 4° C. over 16 hours.

At the end of said time period, precipitated DCU is filtered off, and the reaction mixture is concentrated to dryness.

The so-obtained residue is resuspended with EtOAc and extracted with a solution at 5% of NaHCO$_3$, and with a saturated NaCl solution.

The organic extract is then concentrated to dryness, and the residue is triturated with Et$_2$O, an amount being obtained of 2.189 g (yield 70%), of product as a white powder, which at the chromatographic (TLC and HPLC) analysis does not show impurities, and whose $^1$H-n.m.r. spectrum confirms molecule's structure.

TLC (CMA) $R_F=0.65$
HPLC $T_R=11.95'$ and $12.45'$.

(E) Synthesis of N-[N-(R,S)-α-carbo-β-isopropyl-propanoyl)-triptophan]-(S)-5-amino-2-pyrrolydone. ("L"-gGlp-(R,S)-m-Leu-Trp-OH (Ic).

1.34 g (3.0 mmol) of "L"-g-Glp-(R,S)-m-Leu-Trp-OMe are dissolved in 50 ml of a dioxane-water (4:1 v/v) mixture.

The hydrolysis reaction is carried out at a temperature of 20° C. for three hours, while maintaining solution's pH at the value of 12.5 by means of sequential additions of a mixture of 1M NaOH-dioxane (50/50 v/v).

The preparation is then continued by making the solution neutral (pH 6.5–7.5) with diluted (0.1N) HCl, and diluting it with water.

The two epimers are isolated from freeze-dried product by means of high-pressure preparative liquid chromatography, with the stationary phase being constituted by Lichroprep RP-18 25–40μ resin (Merck), using 0.1% TFA, 26% CH$_3$CN in water as the eluant.

The fractions corresponding to each individual peak are combined, concentrated under reduced pressure, and freeze-dried.

The chromatographic (TLC and HPLC) analysis of isolated products does not show impurity traces, and H-n.m.r. spectrum confirms molecule's structure.

S-isomer:
TLC (CMA) $R_F=0.25$
HPLC: $T_R=7.9'$
R-isomer:
TLC (CMA) $R_F=0.2$
HPLC: $T_R=9.3'$

EXAMPLE 4

Hypotensive effect of GLP-g-Leu-m-TRP-OH (Ia)

Normotensive C.D. male rats from Charles River Co., of weight of 200–300 g, anaesthetized with ethyl urethane (1.75 g/kg by intraperitoneal way) are used. After tracheal cannulating, the right-hand carotid artery is isolated and connected by a cannula to a Hewlett-Packard model 1280 pressure transducer.

From isolated left-hand carotid the arterial flow is recorded by means of Biotronex ® Model BL160 electromagnetic flowmeter.

Other parameters, recorded on Hewlett Packard Model 8824-C polygraph are: pressure variation with time (dp/dt), electrocardiogram (ECG) and BPM (beats per minute).

Tripeptide GLP-g-Leu-m-TRP-OH is dissolved in a mixture constituted by dimethyl-sulphoxide/physiologic solution (1:1 v/v), and injected in the amount of 0.1 ml into right-hand femural vein.

The substance, injected into vein at the dosage of 0.2 mg/kg of body weight, causes a gradual and long-lasting hypotensive effect which reaches a delta of 35 mmHg for diastolic arterial pressure, and of 40 mmHg for systolic arterial pressure.

EXAMPLE 5

Hypotensive effect of g-GLP-D-Leu-m-TRP-OH (Ib)

The test is carried out as in foregoing Example 4, using a dimethyl-sulphoxide:physiologic solution ratio of 1:20 v/v.

The substance, injected into vein at the dosage of 0.2 mg/kg of body weight, causes a gradual hypotensive effect which reaches a delta of 25 mmHg for diastolic arterial pressure, and of 20 mmHg for systolic arterial pressure.

EXAMPLE 6

Hypotensive effect of g-GLP-m-Leu-TRP-OH (Ic)

The test is carried out as in foregoing Example 5, and the substance injected in vein causes a gradual hypotensive effect which reaches a delta of 30 mmHg both for diastolic and systolic arterial pressure.

EXAMPLE 7

Tranquilizer effect of GLP-g-Leu-m-TRP-OH (Ia)

Nine mice of Albino Swiss strain are placed within three different "Activity Cages", and their basal motorial activity is measured during 4 consecutive days. On the fifth day, the compound under test (dissolved in physiologic solution:dimethylsulphoxide 1:1) is administered at the dosage of 10 mg/kg/i.p. At the same time, other 9 mice are treated with the solvent (0.1 ml/10 g of physiologic solution:dimethylsulphoxide 1:1). From the ratios between the records obtained, it is found that this tripeptide inhibits basal motorial activity by 32%.

EXAMPLE 8

Analgesic effect of GLP-g-Leu-m-TRP-OH (Ia)

Twenty female mice of Albino Swiss strain, weighing 25–28 g, were treated with the compound under test, dissolved in physiologic solution:dimethylsulphoxide (1:1), at the dosage of 0.1 ml/kg/i.p. Other 20 mice, of same strain, sex and weight, were treated with the solvent only. After 40 minutes, the acetic acid was administered to both groups, and the increase of writhings was recorded. The compound under test has shown an inhibition of 25% of the number of contorsions.

We claim:

1. Tripeptides having the formulae:

[Structural formulae Ia, Ib, Ic shown]

wherein $R_1$ is

[Structures: CH₂-indole, CH₃-CH-CH₃ with CH₂, or CH₃-CH-CH₂-CH₃]

$R_2$ represents

[Structures: indole-CH₂, benzyl-CH₂, or p-hydroxybenzyl-CH₂]

group; and

Z represents an OH, $OR_3$, $NH_2$, $NHR_3$ group, wherein $R_3$ represents an alkyl group having 1 to 10 carbon atoms.

2. Tripeptides according to claim 1, wherein $R_1$ is

[isopropyl-CH₂ structure]

$R_2$ is

[indolylmethyl structure]

3. Tripeptides according to claim 1, wherein the geminal diaminic residue has S configuration, and the 2-substituted malonyl residue has S configuration.

4. Tripeptides according to claim 1, wherein the geminal diaminic residue has S configuration, and the 2-substituted malonyl residue has R configuration.

5. Tripeptides according to claim 1, wherein the geminal diaminic residue has S configuration, and the 2-substituted malonyl residue is an equimolecular mixture of R and S enantiomers.

6. A pharmaceutical composition useful for the treatment of hypertension, of anxiety and of pain, comprising a pharmaceutically acceptable support, and a therapeutically efficacious amount of one or more tripeptides of the formulae

[Structural formulae Ia and Ib shown]

-continued

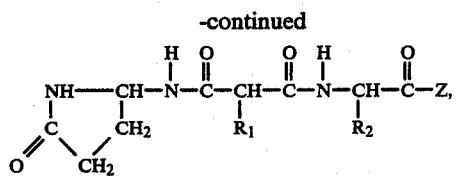   Ic their pharmaceutically acceptable basic salts, esters or alkyl amides;
wherein
$R_1$ is

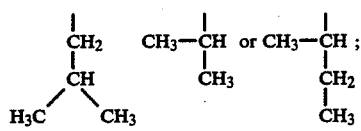

$R_2$ represents

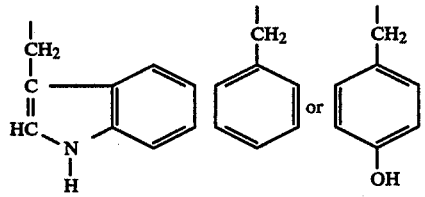

group; and
Z represents an OH, OR$_3$, NH$_2$, NHR$_3$ group, wherein R$_3$ represents an alkyl group having 1 to 10 carbon atoms.

7. A pharmaceutical composition according to claim 6, comprising a diuretic.

8. A method for decreasing blood pressure in mammals, comprising administering a therapeutically efficacious amount of a tripeptide of the formulae

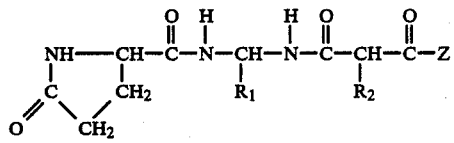   Ia

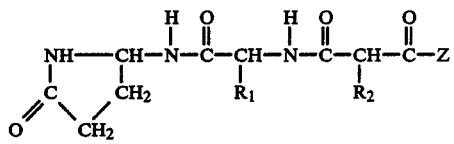   Ib

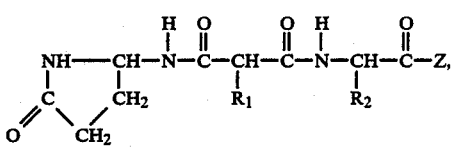   Ic or of a pharmaceutical composition comprising one or more of said tripeptides, to a mammal;
wherein
$R_1$ is

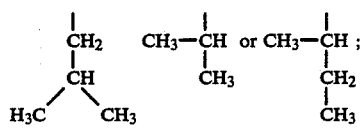

$R_2$ represents

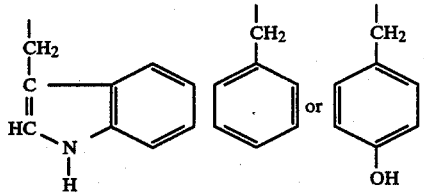

group; and
Z represents an OH, OC$_3$, NH$_2$, NHR$_3$ group, wherein R$_3$ represents an alkyl group having 1 to 10 carbon atoms.

* * * * *